United States Patent
Hammond et al.

(10) Patent No.: US 12,374,448 B2
(45) Date of Patent: *Jul. 29, 2025

(54) QUALITY CONTROL FOR POINT-OF-CARE DIAGNOSTIC SYSTEMS

(71) Applicant: IDEXX Laboratories, Inc., Westbrook, ME (US)

(72) Inventors: Jeremy Hammond, Standish, ME (US); Timothy Butcher, Windham, ME (US); Jui Ming Lin, Falmouth, ME (US); James Russell, North Yarmouth, ME (US)

(73) Assignee: IDEXX LABORATORIES, INC., Westbrook, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/425,540

(22) Filed: Jan. 29, 2024

(65) Prior Publication Data

US 2024/0170141 A1    May 23, 2024

Related U.S. Application Data

(63) Continuation of application No. 17/941,562, filed on Sep. 9, 2022, now Pat. No. 11,887,727, which is a
(Continued)

(51) Int. Cl.
*G16H 40/40* (2018.01)
*G01N 15/01* (2024.01)
(Continued)

(52) U.S. Cl.
CPC ......... *G16H 40/40* (2018.01); *G01N 15/1425* (2013.01); *G01N 15/1429* (2013.01);
(Continued)

(58) Field of Classification Search
CPC .......... G01N 15/1425; G01N 15/1429; G01N 33/48; G01N 33/48742;
(Continued)

(56) References Cited

U.S. PATENT DOCUMENTS

| | | |
|---|---|---|
| 3,909,136 A | 9/1975 | Thomas |
| 4,387,164 A | 6/1983 | Hevey et al. |

(Continued)

FOREIGN PATENT DOCUMENTS

| | | |
|---|---|---|
| CA | 2168452 A1 | 2/1995 |
| EP | 0887637 A2 | 12/1998 |

(Continued)

OTHER PUBLICATIONS

Cembrowski et al., Rationale for using insensitive quality control rules for today's hematology analyzers, Blackwell Publishing Ltd, Int. Jnl. Lab. Hem. 2010, 32, 606-615 (Year: 2010).*
(Continued)

*Primary Examiner* — David L Singer
(74) *Attorney, Agent, or Firm* — Carter, DeLuca & Farrell LLP

(57) ABSTRACT

In aspects, a system includes an on-board storage containing a synthetic quality control material, a plurality of sub-systems having a plurality of operating parameters and including a material analyzer, a database storing quality control results that include results of the material analyzer analyzing the synthetic quality control material over time, one or more processors, and at least one memory storing instructions which, when executed by the one or more processors, cause the system to, automatically without user intervention: generate a control chart based on the quality control results, determine that a parameter of the plurality of operating parameters is out-of-tolerance based on the control chart, and adjust at least one of the plurality of sub-systems
(Continued)

without user intervention to bring the out-of-tolerance parameter to within tolerance.

16 Claims, 4 Drawing Sheets

Related U.S. Application Data continuation of application No. 16/368,929, filed on Mar. 29, 2019, now Pat. No. 11,441,997.

(60) Provisional application No. 62/650,609, filed on Mar. 30, 2018.

(51) Int. Cl.
| | |
|---|---|
| *G01N 15/14* | (2024.01) |
| *G01N 15/1429* | (2024.01) |
| *G01N 35/00* | (2006.01) |
| *G16H 10/40* | (2018.01) |
| *G16H 50/20* | (2018.01) |

(52) U.S. Cl.
CPC .. *G01N 35/00623* (2013.01); *G01N 35/00693* (2013.01); *G16H 10/40* (2018.01); *G16H 50/20* (2018.01); *G01N 15/01* (2024.01)

(58) Field of Classification Search
CPC ....... G01N 33/49–4925; G01N 33/493; G01N 33/5002; G01N 33/5094; G01N 33/62; G01N 33/72–728; G01N 33/80; G01N 33/86; G01N 33/90; G01N 33/96; G01N 2333/96463; G01N 2015/0065; G01N 35/00623; G01N 35/00693; G01N 15/01; G01N 35/00613–2035/00702; G16H 40/20; G16H 40/40; G16H 50/20; G16H 10/40; G16H 10/60
See application file for complete search history.

(56) References Cited

U.S. PATENT DOCUMENTS

| | | | |
|---|---|---|---|
| 4,925,299 A | 5/1990 | Meisberger et al. |
| 4,997,769 A | 3/1991 | Lundsgaard |
| 5,064,282 A | 11/1991 | Curtis |
| 5,074,658 A | 12/1991 | Tavlarides et al. |
| 5,262,329 A | 11/1993 | Carver, Jr. |
| 5,316,725 A | 5/1994 | Carver, Jr. et al. |
| 5,316,951 A | 5/1994 | Carver, Jr. et al. |
| 5,380,491 A | 1/1995 | Carver, Jr. et al. |
| 5,380,663 A | 1/1995 | Schwartz et al. |
| 5,413,732 A | 5/1995 | Buhl et al. |
| 5,463,228 A | 10/1995 | Krause |
| 5,486,477 A | 1/1996 | Carver, Jr. |
| 5,728,351 A | 3/1998 | Carver, Jr. |
| 5,840,254 A | 11/1998 | Carver, Jr. et al. |
| 6,074,879 A | 6/2000 | Zelmanovic et al. |
| 6,184,978 B1 | 2/2001 | Kasdan et al. |
| 6,221,671 B1 | 4/2001 | Groner et al. |
| 6,269,276 B1 | 7/2001 | Akhavan et al. |
| 6,391,263 B1 | 5/2002 | Mishima et al. |
| 6,470,279 B1 | 10/2002 | Samsoondar |
| 6,590,646 B2 | 7/2003 | Kasdan et al. |
| 6,812,032 B1 | 11/2004 | Carver, Jr. et al. |
| 6,887,429 B1 | 5/2005 | Marshall et al. |
| 6,979,569 B1 | 12/2005 | Carver, Jr. et al. |
| 7,294,307 B2 | 11/2007 | Carver, Jr. |
| 7,324,194 B2 | 1/2008 | Roche et al. |
| 7,379,167 B2 | 5/2008 | Mawhirt et al. |
| 7,390,662 B2 | 6/2008 | Riley et al. |
| 7,449,339 B2 | 11/2008 | Samsoondar et al. |
| 7,499,581 B2 | 3/2009 | Tribble et al. |
| 7,590,500 B2 | 9/2009 | Jochum et al. |
| 7,739,060 B2 | 6/2010 | Goebel et al. |
| 7,873,483 B2 | 1/2011 | Miyamoto et al. |
| 7,982,201 B2 | 7/2011 | Bryant et al. |
| 8,086,411 B2 | 12/2011 | Yoshida et al. |
| 8,088,593 B2 | 1/2012 | Burd et al. |
| 8,161,810 B2 | 4/2012 | Cadieux et al. |
| 8,339,586 B2 | 12/2012 | Zahniser et al. |
| 8,381,581 B2 | 2/2013 | Walsh et al. |
| 8,460,528 B2 | 6/2013 | Pollack et al. |
| 8,645,306 B2 | 2/2014 | Hammond |
| 8,664,006 B2 | 3/2014 | Durack et al. |
| 8,668,869 B2 | 3/2014 | Hirayama |
| 8,828,737 B2 | 9/2014 | Gabriel |
| 9,025,145 B2 | 5/2015 | Thomas |
| 9,222,821 B2 | 12/2015 | Walsh et al. |
| 9,322,834 B2 | 4/2016 | Hirayama et al. |
| 11,887,727 B2 | 1/2024 | Hammond et al. |
| 2002/0036142 A1 | 3/2002 | Gascoyne et al. |
| 2003/0030783 A1 | 2/2003 | Roche et al. |
| 2003/0048433 A1 | 3/2003 | Desjonqueres |
| 2003/0092184 A1 | 5/2003 | Young |
| 2003/0097238 A1 | 5/2003 | Harmon |
| 2005/0222504 A1 | 10/2005 | Otvos et al. |
| 2006/0219873 A1 | 10/2006 | Martin et al. |
| 2006/0263905 A1 | 11/2006 | Mishima et al. |
| 2007/0166195 A1 | 7/2007 | Padmanabhan et al. |
| 2007/0217949 A1 | 9/2007 | Mimura et al. |
| 2008/0010019 A1 | 1/2008 | Thomas |
| 2008/0144005 A1 | 6/2008 | Guiney et al. |
| 2008/0187990 A1 | 8/2008 | Nagai et al. |
| 2010/0228491 A1 | 9/2010 | Gutierrez et al. |
| 2011/0207621 A1 | 8/2011 | Montagu et al. |
| 2011/0320174 A1 | 12/2011 | Ragan et al. |
| 2012/0000268 A1 | 1/2012 | Li et al. |
| 2012/0005150 A1 | 1/2012 | Hammond |
| 2012/0230913 A1 | 9/2012 | Johnston et al. |
| 2012/0262703 A1 | 10/2012 | Zahniser et al. |
| 2012/0283975 A1 | 11/2012 | Fukuma |
| 2012/0309636 A1 | 12/2012 | Gibbons et al. |
| 2013/0018618 A1 | 1/2013 | Eshima et al. |
| 2013/0024130 A1 | 1/2013 | Zahniser |
| 2013/0151189 A1 | 6/2013 | Li et al. |
| 2014/0267695 A1 | 9/2014 | Scordato et al. |
| 2014/0324373 A1 | 10/2014 | Xiang et al. |
| 2015/0025808 A1 | 1/2015 | Aguiar |
| 2015/0029492 A1 | 1/2015 | Mpock et al. |
| 2015/0044780 A1 | 2/2015 | Kurz et al. |
| 2015/0331946 A1 | 11/2015 | Balwani |
| 2016/0034653 A1 | 2/2016 | Kuchipudi et al. |
| 2016/0320420 A1 | 11/2016 | Yundt-Pacheco et al. |
| 2016/0356800 A1 | 12/2016 | Glavina et al. |
| 2017/0261526 A1 | 9/2017 | Calatzis et al. |
| 2017/0285624 A1 | 10/2017 | Lesher |
| 2018/0209999 A1 | 7/2018 | Han |
| 2019/0271713 A1 | 9/2019 | Heinemann et al. |
| 2019/0346466 A1 | 11/2019 | Fujimoto et al. |

FOREIGN PATENT DOCUMENTS

| | | |
|---|---|---|
| EP | 2402765 A2 | 1/2012 |
| EP | 2685264 A2 | 1/2014 |
| GB | 2347234 A | 8/2000 |
| JP | H1183724 A | 3/1999 |
| JP | 2004506876 A | 3/2004 |
| JP | 2011237462 A | 11/2011 |
| JP | 2012013704 A | 1/2012 |
| JP | 2016045004 A | 4/2016 |
| JP | 2016530620 A | 9/2016 |
| JP | 2017161526 A | 9/2017 |
| WO | 0194938 A1 | 12/2001 |
| WO | 2016046522 A1 | 3/2016 |
| WO | 2018099859 A1 | 6/2018 |
| WO | 2018142871 A1 | 8/2018 |

(56) References Cited

OTHER PUBLICATIONS

Office Action issued in corresponding MX Patent Application No. MX/a/2020/009199 dated May 22, 2024, pp. 1-15, with English translation.
Beckman Coulter, CytoFLEX Flow Cytometer Instructions for Use (Year: 2015).
Biehl et al., "Gaps and Challenges of Point-of-Care Technology", IEEE Sensors Journal, vol. 8, No. 5, May 2008.
Examination Report dated Jun. 23, 2021, by the Australian Intellectual Property Office in counterpart Australian Patent Application No. 2019243592, pp. 1-3 (Year: 2021).
Examination Report dated Mar. 28, 2022, by the Australian Intellectual Property Office in counterpart Australian Patent Application No. 2019243592, pp. 1-3.
IDEXX Laboratories, IDEXX ProCyte Dx Hematology Analyzer Operator's Guide (Year: 2014).
IDEXX, LaserCyte Dx/IDEXX LaserCyte Hematology Analyzer Operator's Guide (Year: 2014).
IDEXX, VetLab Station Operator's Guide (Year: 2014).
International Search Report and Written Opinion issued by the European Patent Office acting as International Searching Authority in corresponding International Application No. PCT/US2019/024735 dated Aug. 5, 2019.
Japanese Office Action dated Nov. 2, 2021, by the Japanese Intellectual Property Office in counterpart Japanese patent application No. 2020-550149, pp. 1-5.
Lehe et al, Evaluating Operational Specifications of Point-of-Care Diagnostic Tests: A Standardized Scorecard, Oct. 2012 |; vol. 7| Issue 10 | e47459 (Year: 2012).
Nourse et al, Engineering of a miniaturized, robotic clinical laboratory, Bioengineering & Translational Medicine 2018; 3: 58-70 ( Year: 2018).
Office Action issued in corresponding JP Patent Application No. 2020-550149 dated Jun. 21, 2022, pp. 1-11.
Canadian Office Action issued in corresponding CA Patent Application No. 3,095,020, dated Aug. 31, 2022, pp. 1-6.
Coakley, K.J. et al., "Secondary ion mass spectrometry measurements of isotopic ratios: correction for time varying count rate" International Journal of Mass Spectrometry (Jan. 2005) pp. 107-120, vol. 240, Issue 2.
Chinese Office Action issued in corresponding CN Patent Application No. 201980019032.7, dated Aug. 17, 2023, with English translation.
EP Office Action issued in corresponding EP Patent Application No. 19722271.4 dated Dec. 7, 2023, pp. 1-6.
Office Action issued in corresponding MX Patent Application No. MX/a/2020/009199 dated Nov. 27, 2024, pp. 1-14, with English translation.

\* cited by examiner

QUALITY CONTROL FOR POINT-OF-CARE DIAGNOSTIC SYSTEMS

CROSS REFERENCE TO RELATED APPLICATIONS

The present application is a continuation of U.S. patent application Ser. No. 17/941,562, filed on Sep. 9, 2022, now U.S. Pat. No. 11,887,727, which is a continuation of U.S. patent application Ser. No. 16/368,929, filed on Mar. 29, 2019, now U.S. Pat. No. 11,441,997, which claims the benefit of and priority to U.S. Provisional Patent Application No. 62/650,609, filed on Mar. 30, 2018. The entire contents of each of the foregoing applications are hereby incorporated herein by reference.

TECHNICAL FIELD

The present disclosure relates to medical diagnostics, and more particularly, to quality control for point-of-care medical diagnostic systems.

BACKGROUND

Medical guidance for many medical diagnostic systems, such as hematology analyzers, recommends analyzing a sample as soon as possible after drawing the sample. This recommendation can be difficult if the sample is obtained at the point of care but the test is to be performed at an external laboratory. Therefore, many doctors and veterinarians prefer to have point-of-care (POC) systems to analyze fresh samples. On the other hand, medical diagnostic systems rely on quality control procedures to confirm system functionality and assure result accuracy. However, quality control procedures may not be familiar to POC offices, and this lack of familiarity can be a significant reason for doctors and veterinarians to send samples to external laboratories.

Hematology diagnostic systems have some of the most difficult requirements for quality control and performance. Quality control (QC) for hematology systems can be especially difficult because there is a general belief in the medical and veterinary fields that hematology QC must use fixed cells in order to accurately gauge system performance. Fixed cell quality control generally involves cells that have been stabilized and mixed in predetermined concentrations. The cells can be human or veterinary cells, which are commonly used to represent different cell types in whole blood.

The primary approach for hematology QC using fixed-cells generally requires refrigerated storage, with the fixed cells having a shelf-life of about eight-weeks. Additionally, fixed-cells have limited stability at room temperature, and thus, the operator must warm the sample prior to use and then return them to cold storage as soon as possible thereafter. Also, after opening, fixed cells generally remain stable for about two-weeks or less. The short shelf life and strict thermal requirements of fixed cells often create doubt about the material when a QC test fails, requiring reruns with a separate lot of control material to confirm the result. Another disadvantage of fixed cells is that hematology systems are designed to interact with cells in a particular chemical manner, and such interactions can be inhibited by techniques used to stabilize cells for fixed-cell controls.

For veterinary diagnostic systems, fixed-cell quality control approaches often have deficiencies when several veterinary species are supported. For veterinary diagnostics, there can be significant differences between cells of different species, and therefore, each species will generally have its own cell recognition algorithm in the diagnostic system. In such systems, fixed cell quality control materials may not be able to confirm system performance for all supported species. For example, canine sample analysis could satisfy quality control parameters, while feline sample analysis may not. In particular, fixed-cell quality control approaches may not be able to confirm the performance of certain system components, such as species-specific reagent reactions and species-specific fluidic and detection system problems.

Accordingly, there is continuing interest in improving medical diagnostic systems.

SUMMARY

The present disclosure relates to quality control for point-of-care diagnostic systems. In accordance with aspects of the present disclosure, an integration of on-board automated bead analysis, automated blank runs, and/or trended patient samples (by species), provides a new approach to determine not only that the diagnostic system is in control, but also which component is failing if it is not in control.

In accordance with aspects of the present disclosure, a system for point-of-care medical diagnostics includes an on-board storage containing a synthetic quality control material, a plurality of sub-systems having a plurality of operating parameters where the sub-systems include a material analyzer configured to analyze patient samples and to analyze the synthetic quality control material, a database storing quality control results over time where the quality control results include results of the material analyzer analyzing the synthetic quality control material over time, one or more processors, and at least one memory storing instructions which, when executed by the one or more processors, cause the system to, automatically without user intervention: generate a control chart based on the quality control results, determine that a parameter of the plurality of operating parameters is out-of-tolerance based on the control chart, and adjust at least one of the plurality of sub-systems without user intervention to bring the out-of-tolerance parameter to within tolerance. In various embodiments, the instructions, when executed by the one or more processors, cause the system to provide a visual indication to an operator regarding the automatic adjustment.

In various embodiments, the database stores previous patient test results that include results of the material analyzer analyzing samples obtained from a plurality of patients over time. The instructions, when executed by the one or more processors, cause the system to, automatically without user intervention: generate another control chart based on the previous patient test results, determine that another parameter of the plurality of operating parameters is out-of-tolerance based on the another control chart, and adjust at least one sub-system of the plurality of sub-systems without user intervention to bring the another out-of-tolerance parameter to within tolerance.

In various embodiments, the instructions, when executed by the one or more processors, cause the system to, automatically without user intervention: determine that another parameter of the plurality of operating parameters is out-of-tolerance, determine that the another out-of-tolerance parameter requires user intervention to bring the another out-of-tolerance parameter to within tolerance, and provide a visual indication informing an operator that the another parameter is out-of-tolerance.

In various embodiments, the instructions, when executed by the one or more processors, cause the system to, automatically without user intervention: analyze a blank sample using the material analyzer where the material analyzer operates on the blank sample in a same manner that the material analyzer operates on a patient sample, determine that the material analyzer should be cleaned based on the analysis of the blank sample, and provide a visual indication informing an operator that the material analyzer should be cleaned.

In various embodiments, the instructions, when executed by the one or more processors, cause the system to, automatically without user intervention: access the synthetic quality control material from the on-board storage, analyze the synthetic quality control material using the material analyzer to provide additional quality control results, and store the additional quality control results in the database.

In various embodiments, the material analyzer is a hematology analyzer. In various embodiments, the material analyzer is at least one of: a chemistry analyzer, a coagulation analyzer, or a urine analyzer.

In various embodiments, the material analyzer includes a flow cytometer. In various embodiments, the plurality of sub-systems includes a fluidics sub-system, an optics sub-system, and an electronics sub-system. In various embodiments, the plurality of operating parameters include optical density, flow rate, extinction channel (EXT), low angle forward light scatter channel (FSL), right angle scatter channel (RAS), high angle forward light scatter channel (FSH), and time-of-flight channel (TOF).

In accordance with aspects of the present disclosure, a system for point-of-care medical diagnostics includes an on-board storage containing a synthetic quality control material, a plurality of sub-systems having a plurality of operating parameters and including a material analyzer configured to analyze patient samples and to analyze the synthetic quality control material, a database, one or more processors, and at least one memory. The database stores data including quality control results over time that include results of the material analyzer analyzing the synthetic quality control material over time, previous patient test results that include results of the material analyzer analyzing samples obtained from a plurality of patients over time, and blank sample results over time that include results of the material analyzer analyzing blank samples over time. The at least one memory stores instructions which, when executed by the one or more processors, cause the system to, automatically without user intervention: generate at least one control chart based on the quality control results, the previous patient test results, and the blank sample results, determine that a parameter of the plurality of operating parameters is out-of-tolerance based on the at least one control chart, and adjust at least one sub-system of the plurality of sub-systems without user intervention to bring the out-of-tolerance parameter to within tolerance.

Further details and aspects of exemplary embodiments of the present disclosure are described in more detail below with reference to the appended figures.

DETAILED DESCRIPTION

The present disclosure relates to quality control for point-of-care medical diagnostic systems. As used herein, point-of-care refers to a location where care is provided to human or animal patients, and a medical diagnostic system refers to a system that can analyze a sample obtained from a patient to diagnose a medical condition of the patient. Accordingly, a medical diagnostic system includes a patient sample analyzer, such as, but not limited to, a flow cytometer.

Quality control in general involves having a diagnostic system demonstrate its performance on quality control (QC) materials, such that appropriate performance on the QC materials correlates to appropriate performance on patient samples. As will be described in detail herein, the proposed systems and methods relate to quality control operations using synthetic QC materials, patient-based quality control, and/or blank runs. Portions of the present disclosure will focus on veterinary hematology analyzers, but the description herein applies to other types of medical diagnostic systems as well, including, but not limited to, chemistry analyzers, coagulation analyzers, and urine analyzers.

Figure 1:
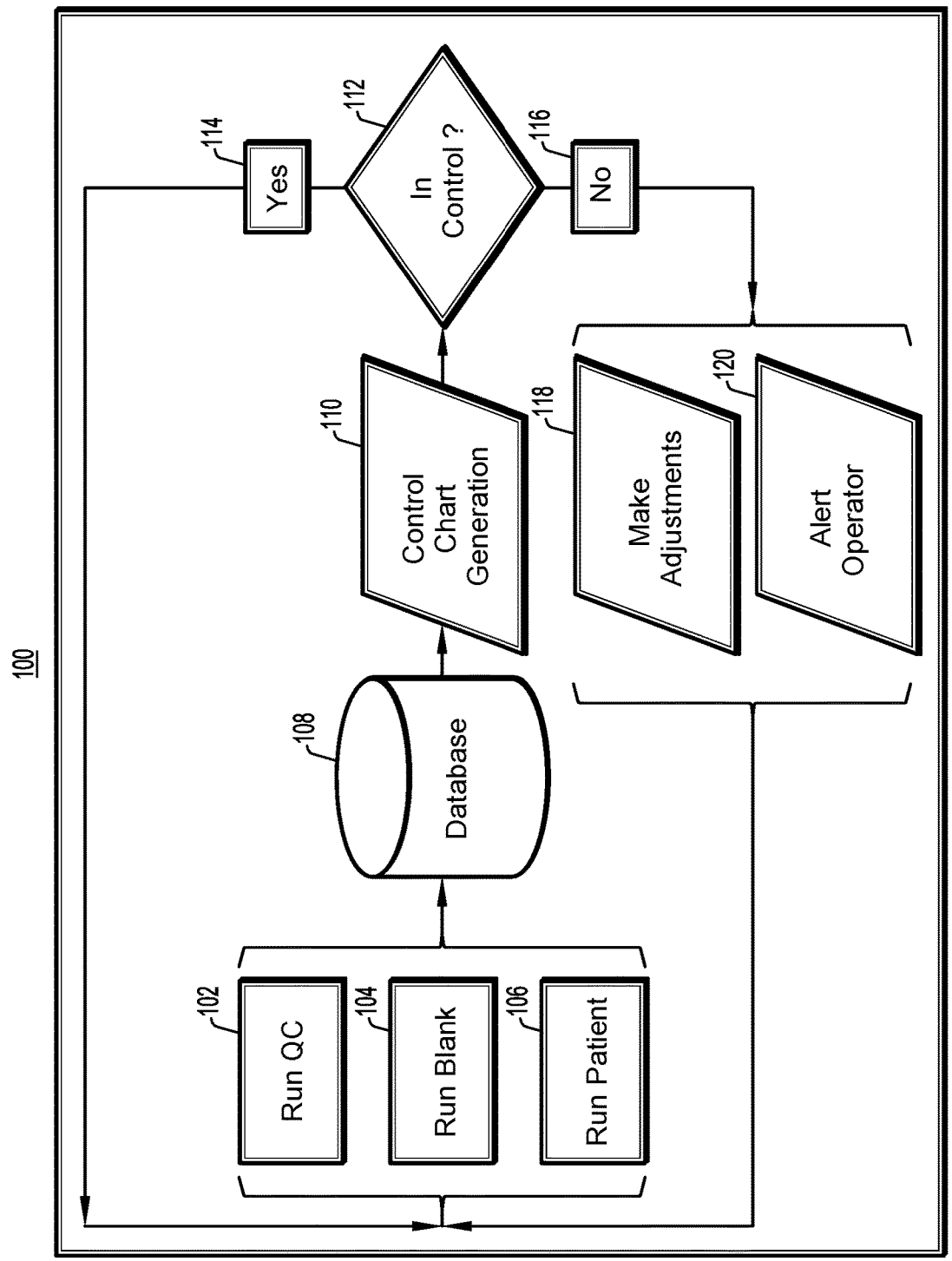
FIG. 1 is a block diagram of an embodiment of quality control operations, in accordance with aspects of the present disclosure.

Referring to FIG. 1, there is shown a block diagram of an embodiment of exemplary quality control procedures 100 for a medical diagnostic system. The quality control procedures 100 include a QC operation 102, a blank run operation 104, and/or a patient-data operation 106. Each of these operations 102-106 will be described in more detail later herein. The results of these operations 102-106 are stored in a database 108, and the information in the database 108 is then used to generate control charts 110. Control charts will be described in more detail later in connection with FIG. 2. Based on the control charts 110, the quality control procedures can determine whether various components of the medical diagnostic system are operating within intended parameters 112. If the system is operating within intended parameters 114, no adjustments are needed, and the system can run the quality control operations 102-106 again when scheduled or requested to do so. If the system is not operating within intended parameters 116, the system can automatically make adjustments where possible 118, and/or can alert an operator to manually make adjustments when automatic adjustments are not possible 120.

The following describes the quality control run 102 of FIG. 1. The blank run 104 and then patient run 106 will be described later herein.

A quality control run 102 involves the use of quality control (QC) materials. In accordance with aspects of the present disclosure, a QC material is provided that is a synthetic non-biological material, but still provides sensor responses that mimic or that are similar to sensor responses for biological materials. In various embodiments, because the QC materials are synthetic, they can have longer shelf life than fixed cells. In various embodiments, the QC material is stable at room temperature and can be stored on-board the diagnostic system at room temperature. In various embodiments, the diagnostic system can store the on-board QC material at specified environmental conditions (such as refrigeration or otherwise), and then handle them appropriately (e.g., warm the material) when an automated run is desired. In various embodiments, no action from the operator is needed to perform the quality control operations other than replenishing the on-board control material as needed.

In various embodiments, the QC material can be polymer beads for standardization and calibration of a hematology flow cytometer. An example of polymer beads is disclosed in U.S. Pat. No. 6,074,879, which is hereby incorporated by reference herein in its entirety, and which persons skilled in the art will understand. In various embodiments, the polymer beads can include latex, polystyrene, polycarbonate, and/or methacrylate polymers.

In a fixed-cell quality control material, even though the cells are surrogates for natural patient cells, they have different chemical behavior compared to actual cells in natural samples. Accordingly, in the medical diagnostic system, the classification of fixed-cells is performed differently than the classification of patient samples, to account for these differences. In contrast, in accordance with aspects of the present disclosure, the QC material can mimic or substantially resemble the cellular or chemical features that the medical diagnostic system is intended to count, measure, or analyze, such that the same classification methodology can be used for natural samples as well as for the QC materials of the present disclosure.

In accordance with aspects of the present disclosure, the diagnostic system can automatically run the quality control operations 102-106. For example, the diagnostic system can include a feedback sub-system 100 that works with the QC materials housed within the diagnostic system. Based on the QC materials and the feedback sub-system, the diagnostic system can determine whether its components are functioning within intended parameters or whether adjustments are required. In various embodiments, some adjustments can be performed automatically 118 by the diagnostic system. Such automatic adjustments can beneficially maintain diagnostic accuracy and preempt significant diagnostic errors. Other adjustments may require user interaction, and the diagnostic system can provide an indication to the user regarding any such actions 120. Thus, the user receives the benefits of automated alerts with actionable guidance to maintain the diagnostic system. In various embodiments, the diagnostic system can provide an indication to the user regarding the diagnostic system's performance based on the quality control operations 102-106.

In various embodiments, for adjustments that cannot be automatically performed, the diagnostic system can communicate an electronic message or report to the manufacturer or servicer for the diagnostic system. The manufacturer or servicer can use such electronic messages/reports in various ways. In various embodiments, the electronic messages can be used to schedule service for the diagnostic system. In various embodiments, the electronic messages can be aggregated for multiple diagnostic systems and can be analyzed to determine performance trends of various components of the diagnostic systems. Such information can be useful for identifying areas that may benefit from design modifications or improvements.

In various embodiments, quality control procedures 100 can be automatically performed each day to keep the diagnostic system well-maintained. For example, the quality control procedures 100 can automatically be performed at 2:00 AM each day, or at another time. Automated hematology analyzers in human medicine can perform quality control procedures 100 at least once per 8-hour shift, which is the frequency generally required by governing agency regulation. Veterinary hematology analyzers do not have regulatory requirements for quality control. Accordingly, veterinary offices may perform quality control procedures 100 less often. In various embodiments, the frequency of running the quality control procedures 100 may depend on how often or how seldom patient samples are analyzed. For example, veterinary offices may run very few patient samples in a day, or as few as one sample per day. In such offices, running quality control procedures 100 once per day would double the cost of reagents used by the office. Accordingly, for such offices, the frequency of running the quality control procedures 100 may be less frequent. In various embodiments, veterinary hematology analyzers may perform quality control analyses as infrequently as once per month.

In accordance with aspects of the present disclosure, information relating to the quality control tests 102-106 can be stored in the database 108. The database can be any type of database, such as a SQL database, a NoSQL database, or another type of database.

Figure 2:
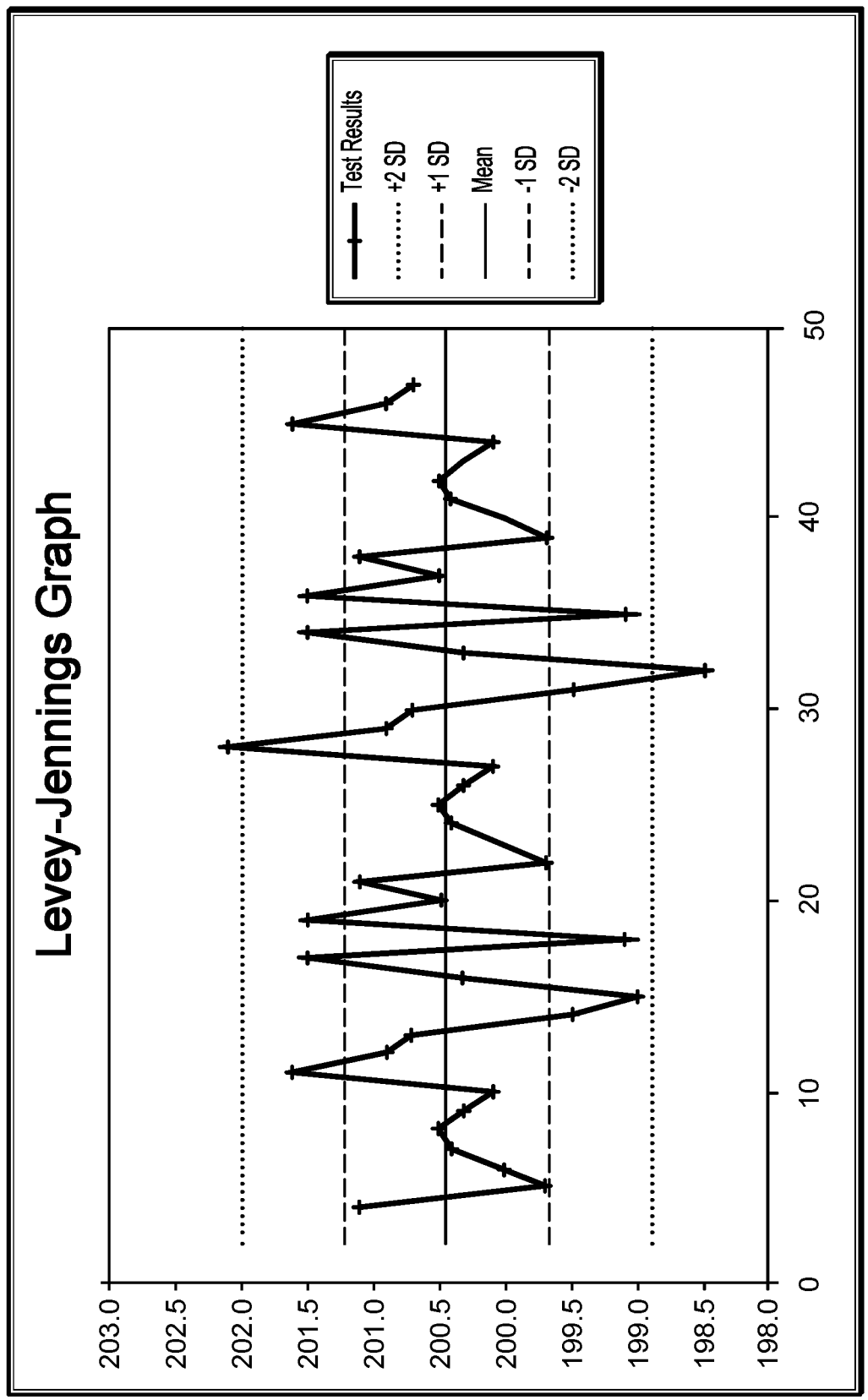
FIG. 2 is a diagram of an exemplary control chart used for quality control, in accordance with aspects of the present disclosure.

In various embodiments, QC results can be plotted in control charts 110, such as a Levey-Jennings chart as shown in FIG. 2, and can be compared with target values or ranges. In various embodiments, control chart rules can determine whether the system is in control or not 112. In various embodiments, a control chart 110 can be generated for multiple parameters to determine which parameter or parameters may be out of control and require corrective action 116, and which parameters are in control and require no changes 114.

In various embodiments, the quality control materials can be provided in predetermined concentrations that enable three levels of control, including normal, high, and low levels. Having three levels allows the user to confirm whether the diagnostic system is functioning properly to detect the normal range and the abnormal ranges. In various embodiments, each level can be shown in the control chart. The control charts can demonstrate the historical performance of the analyzer, as shown in FIG. 2, and can provide a way to detect when changes are needed, including relatively small changes. In various embodiments, the operator can have the ability to access and view the control charts. In various embodiments, a control chart need not be in the form of a chart as shown in FIG. 2, and can be implemented in different ways. For example, in various embodiments, a control chart can be implemented as an organization of stored data values that are correlated with time or correlated with data sample number.

In various embodiments, calibration needs can be determined from the control chart data. A technician can determine if an out-of-control parameter requires a diagnostic system component to be re-calibrated, or whether other actions should be taken instead, such as cleaning the component. Generally, calibration changes are performed last, after all other functionality is confirmed.

Accordingly, described above herein are various aspects of quality control for medical diagnostic systems in general. The following will describe aspects of flow-cytometry-based diagnostic systems in particular, and quality control for such systems. An example of a flow-cytometry-based analyzer is shown and described in U.S. Pat. No. 7,324,194, which is hereby incorporated by reference herein in its entirety, and which persons skilled in the art will understand.

Figure 3:
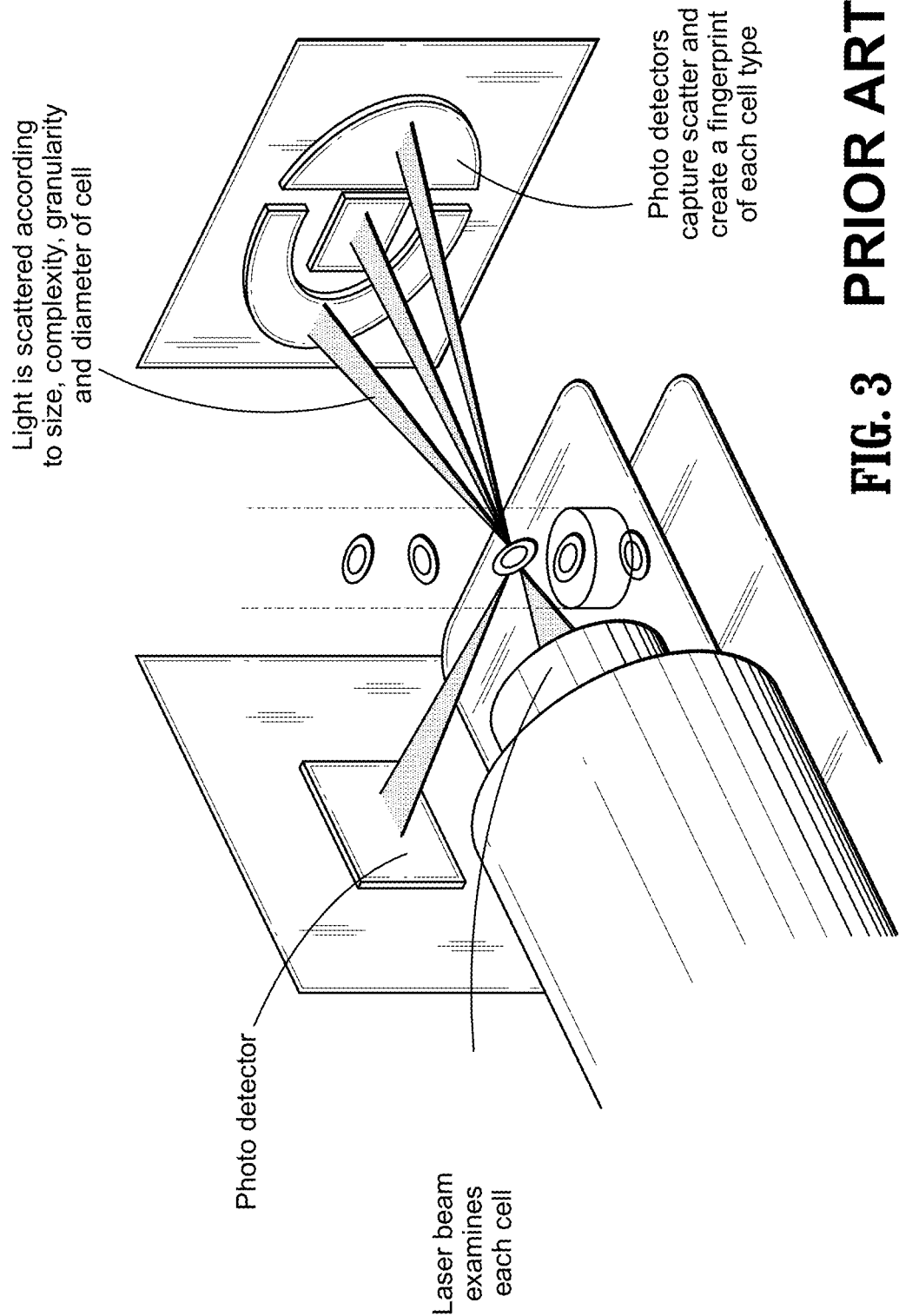
FIG. 3 is a diagram of exemplary components of a flow cytometry analyzer, in accordance with aspects of the present disclosure.
Figure 4:
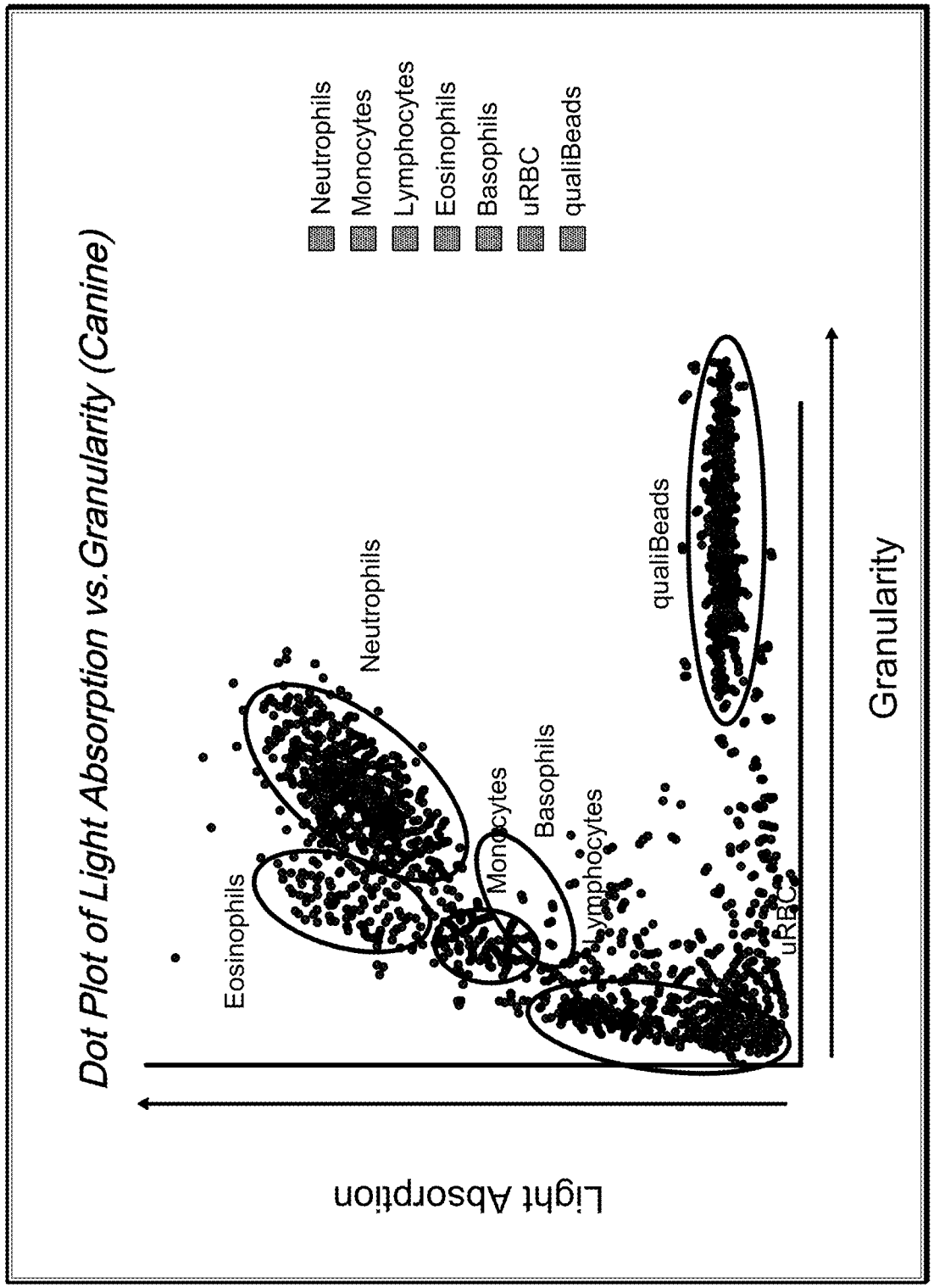
FIG. 4 is a diagram of an exemplary plot of optical characteristics for various particles, in accordance with aspects of the present disclosure.

Flow cytometry systems include sub-systems such as fluidics, optics, and electronics sub-systems. Referring to FIG. 3, a fluidics sub-system arranges a sample into a stream of particles, such as a stream of cells. The optics sub-system examines each cell by directed a laser beam to each cell and detecting scattered light using photo-detectors. Light is scattered according to size, complexity, granularity, and diameter of the cells, which form a "fingerprint" of each cell type. An example is shown in FIG. 4. The electronics sub-system can process the fingerprints to classify, count, and/or otherwise analyze the cells/particles in the sample stream.

Flow cytometry systems have a series of settings and parameters that tune the fluidics, optics, and electronics sub-systems so that specific scatter patterns and positions will be produced from input samples. When these sub-systems all function properly, the system is able to correlate the scatter outputs with particular cells using recognition algorithms. However, if these parameters shift, the recognition algorithms can fail. Another level of tuning is part of the calibration process, where various calibration parameters are used to tune output results to match reference values for a given set of samples. As the diagnostic system drifts or shifts, the calibration parameters may need to be adjusted to ensure that output results continue to match reference values.

In accordance with aspects of the present disclosure, a flow cytometer for hematology can utilize quality control procedures (FIG. 1, 100) to ensure that the major functions of the diagnostic system are operating in a controlled manner, including yielding accurate and precise results. The following aspects and parameters of a hematology system can be tested and trended by the quality control procedures of FIG. 1.

Preanalytic: is the sample appropriately mixed. In various embodiments, mixing of a quality control material can be performed by an internal vortex mixer in the medical diagnostic system. The vortex mixer can mix the quality control material from several seconds, such as 15 seconds, to several minutes, such as 15 minutes.

Dilution: does the system make the correct dilution, including sample volume, reagent volume, and mixing. In various embodiments, aspects of a flow cytometry system such as optical density can be tested. In various embodiments, optical density can be tested using a colored dye sample, such as red dye.

System Chemistry: do the reagents interact appropriately with the sample.

Fluidics: does the diluted sample present to the detection method appropriately. In various embodiments, aspects of a flow cytometry system such as flow rate can be tested.

Sensors: do the cells interact with the detection system in the proper manner. In various embodiments, aspects of a flow cytometry system such as extinction channel (EXT), low angle forward light scatter channel (FSL), right angle scatter channel (RAS), high angle forward light scatter channel (FSH), and/or time-of-flight channel (TOF), can be tested.

Signal Processing: do the cell signals present with appropriate signal to noise.

Classification Algorithm: do the cells present appropriately to the detection system so that the algorithm identifies the populations correctly.

Results: does the system provide precise and accurate results.

The following will now describe the blank run operation 104 of FIG. 1. The fluidic sub-system of a flow cytometer is responsible for combining whole blood samples with reagents, mixing them, and moving them to the laser optics sub-system. The fluidic sub-system of a flow cytometer always contains reagents and generally requires maintenance procedures to ensure it is ready to run a sample. When a diagnostic system has one run per day or one run every few days, the fluidic sub-system is at risk of becoming "dirty" from, for example, protein, bacteria, stain, or salt concentrations in the fluid lines. In accordance with aspects of the present disclosure, periodic flushes can be performed to keep the fluidic sub-system clean. In various embodiments, the periodic flushes can be performed by using "blank" runs, which are diagnostic system runs that are performed as though a sample is present, but without any sample actually being present. The results of these blank runs can be recorded 108 and charted 110 to determine cleanliness of the fluidic sub-system and to evaluate any trends in the recorded data. In various embodiments, blank nm operations 104 can be performed automatically by the diagnostic system on a regular basis or as scheduled or requested. Because blank runs are performed as though a sample is present, reagents are used in blank runs and are consumed more quickly.

Blank runs 104 can measure cleanliness of the diagnostic system and ensure there is no sample carryover from one run to the next. In particular, in a blank run, diagnostic system sensor values will shift if there is buildup in the optical path or other wear conditions in various components. Trending of the blank run data allows for an ongoing cleanliness checks using historical trends. Some cleanliness problems can be corrected. For example, operator can run a bleach sample in the diagnostic system to remove buildup in the optical path, or can run a biocide sample to kill bacteria colonies that may have infiltrated the diagnostic system. Thus, the blank run 104 can identify such conditions and alert an operator to actions to address such conditions. In various embodiments, some diagnostic system measurements can use the blank run as a reference to self-calibrate results, such as in the transmittance measurement for hemoglobin where the blank value is used in a ratio with the sample value to determine the optical transmittance in accordance with Beer's Law.

The following will describe aspects of the patient data run 106 of FIG. 1. Non-fresh sample control approaches have limited capacity to evaluate reagent chemistry and algorithm effects. In view of such limitations, and in accordance with aspects of the present disclosure, quality control procedures can be augmented with feedback control approaches based on patient-data of multiple patients. An example of using patient data to determine normal and abnormal data ranges is described in U.S. Patent Application Publication No. 2015/0025808, which is hereby incorporated by reference herein in its entirety, and which persons skilled in the art will understand.

In various embodiments, the patient run operation 106 involves averaging sequential patient samples using various averaging techniques to determine data ranges and trends based on patient samples. This data can be stored in the database 108 and can be used to generate control chart 110. In various embodiments, control chart rules 112 can be applied to determine if the diagnostic system is in or out of control by comparing a patient sample result to the patient-data-based control chart. In various embodiments, patient run operations 106 for quality control purposes can be performed automatically by the diagnostic system on a regular basis or as scheduled or requested.

In various embodiments, a separate control chart 110 can be generated for each animal species supported by the diagnostic system, such as a canine control chart, or a feline control chart. In various embodiments, calibration adjustments can be performed based on the species-specific population results.

Accordingly, described herein is an integration of on-board automated bead analysis, automated blank runs, and/or trended patient samples (by species), which provides a new approach to determine not only that the diagnostic system is in control, but also which component is failing if it is not in control. Actionable guidance can be automatically provided to operators if manual interaction is required. Or if the diagnostic system can be automatically adjusted to fall within intended parameters, the diagnostic system will perform the automatic adjustment and inform the operator accordingly.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure Like reference numerals may refer to similar or identical elements throughout the description of the figures.

The phrases "in an embodiment," "in embodiments," "in various embodiments," "in some embodiments," "in various embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, Matlab, operating system command languages, Pascal, Perl, PL1, Python, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may be located within a device or system at an end-user location, may be located within a device or system at a manufacturer or servicer location, or may be a cloud computing processor located at a cloud computing provider. The controller may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A method for operating a system for point-of-care medical diagnostics, the system comprising:
    an on-board storage container storing a consumable synthetic quality control material at room temperature for automatic use by quality control operations over time, the consumable synthetic quality control material configured to provide flow cytometry sensor responses resembling flow cytometry sensor responses for cellular or chemical features of blood;
    a plurality of sub-systems having a plurality of operating parameters, the sub-systems including a flow cytometry hematology analyzer configured to analyze patient samples and to analyze the consumable synthetic quality control material; and
    a database storing quality control results over time, the quality control results including results of the flow cytometry hematology analyzer analyzing the consumable synthetic quality control material over time;

the method comprising, automatically without user intervention:
  performing the automatic quality control operations over time by accessing the consumable synthetic quality control material from the on-board storage container over time and analyzing the consumable synthetic quality control material over time using the flow cytometry hematology analyzer to generate the quality control results over time;
  storing the quality control results in the database over time;
  generating a control chart based on the quality control results stored in the database;
  determining that a parameter of the plurality of operating parameters is out of tolerance based on the control chart; and
  adjusting at least one of the plurality of sub-systems without user intervention to bring the out-of-tolerance parameter to within tolerance.

2. The method of claim 1, wherein the database further stores previous patient test results, the previous patient test results including results of the flow cytometry hematology analyzer analyzing samples obtained from a plurality of patients over time,
  the method further comprising, automatically without user intervention:
    generating another control chart based on the previous patient test results;
    determining that another parameter of the plurality of operating parameters is out-of-tolerance based on the another control chart; and
    adjusting at least one sub-system of the plurality of sub-systems without user intervention to bring the another out-of-tolerance parameter to within tolerance.

3. The method of claim 1, further comprising providing a visual indication to an operator regarding an automatic adjustment.

4. The method of claim 1, further comprising, automatically without user intervention:
  determining that another parameter of the plurality of operating parameters is out-of-tolerance;
  determining that the another out-of-tolerance parameter requires user intervention to bring the another out-of-tolerance parameter to within tolerance; and
  providing a visual indication informing an operator that the another parameter is out-of-tolerance.

5. The method of claim 1, further comprising, automatically without user intervention:
  analyzing a blank sample using the flow cytometry hematology analyzer, wherein the flow cytometry hematology analyzer operates on the blank sample in a same manner that the flow cytometry hematology analyzer operates on a patient sample;
  determining that the flow cytometry hematology analyzer should be cleaned based on the analysis of the blank sample; and
  providing a visual indication informing an operator that the flow cytometry hematology analyzer should be cleaned.

6. The method of claim 1, wherein the hematology analyzer includes at least one of: a chemistry analyzer, or a coagulation analyzer.

7. The method of claim 1, wherein the plurality of sub-systems includes a fluidics sub-system, an optics sub-system, and an electronics sub-system.

8. The method of claim 7, wherein the plurality of operating parameters includes optical density, flow rate, extinction channel (EXT), low angle forward light scatter channel (FSL), right angle scatter channel (RAS), high angle forward light scatter channel (FSH), and time-of-flight channel (TOF).

9. A method for operating a system for point-of-care medical diagnostics, the system comprising:
  an on-board storage container storing a consumable synthetic quality control material at room temperature for automatic use by quality control operations over time, the consumable synthetic quality control material configured to provide flow cytometry sensor responses resembling flow cytometry sensor responses for cellular features of blood;
  a plurality of sub-systems having a plurality of operating parameters, the sub-systems including a flow cytometry hematology analyzer configured to analyze patient samples and to analyze the consumable synthetic quality control material;
  a database storing data including:
    quality control results over time, the quality control results including results of the flow cytometry hematology analyzer analyzing the consumable synthetic quality control material over time,
    previous patient test results, the previous patient test results including results of the flow cytometry hematology analyzer analyzing samples obtained from a plurality of patients over time, and
    blank sample results over time, the blank sample results including results of the flow cytometry hematology analyzer analyzing blank samples over time;
  the method comprising, automatically without user intervention:
  performing the automatic quality control operations over time by accessing the consumable synthetic quality control material from the on-board storage container over time and analyzing the consumable synthetic quality control material over time using the flow cytometry hematology analyzer to generate the quality control results over time;
  storing the quality control results in the database over time;
  generating at least one control chart based on the quality control results, the previous patient test results, and the blank sample results stored in the database;
  determining that a parameter of the plurality of operating parameters is out-of-tolerance based on the at least one control chart; and
  adjusting at least one sub-system of the plurality of sub-systems without user intervention to bring the out-of-tolerance parameter to within tolerance.

10. The method of claim 9, wherein the database further stores previous patient test results, the previous patient test results including results of the flow cytometry hematology analyzer analyzing samples obtained from a plurality of patients over time,
  the method further comprising, automatically without user intervention:
    generating another control chart based on the previous patient test results;
    determining that another parameter of the plurality of operating parameters is out-of-tolerance based on the another control chart; and adjusting at least one sub-system of the plurality of sub-systems without user intervention to bring the another out-of-tolerance parameter to within tolerance.

11. The method of claim 9, further comprising providing a visual indication to an operator regarding an automatic adjustment.

12. The method of claim 9, further comprising, automatically without user intervention:

determining that another parameter of the plurality of operating parameters is out-of-tolerance;

determining that the another out-of-tolerance parameter requires user intervention to bring the another out-of-tolerance parameter to within tolerance; and providing a visual indication informing an operator that the another parameter is out-of-tolerance.

13. The method of claim 9, further comprising, automatically without user intervention:

analyzing a blank sample using the flow cytometry hematology analyzer, wherein the flow cytometry hematology analyzer operates on the blank sample in a same manner that the flow cytometry hematology analyzer operates on a patient sample;

determining that the flow cytometry hematology analyzer should be cleaned based on the analysis of the blank sample; and providing a visual indication informing an operator that the flow cytometry hematology analyzer should be cleaned.

14. The method of claim 9, wherein the hematology analyzer includes at least one of: a chemistry analyzer, or a coagulation analyzer.

15. The method of claim 9, wherein the plurality of sub-systems includes a fluidics sub-system, an optics sub-system, and an electronics sub-system.

16. The method of claim 15, wherein the plurality of operating parameters includes optical density, flow rate, extinction channel (EXT), low angle forward light scatter channel (FSL), right angle scatter channel (RAS), high angle forward light scatter channel (FSH), and time-of-flight channel (TOF).

* * * * *